United States Patent [19]

Eliades et al.

[11] 4,073,744

[45] Feb. 14, 1978

[54] NITRITE BASED RUST INHIBITOR COMPLEX

[75] Inventors: Theo Ioannou Eliades; Noemi Bernardo Ramirez, both of Scarborough, Canada

[73] Assignee: Surpass Chemicals Limited, Scarborough, Canada

[21] Appl. No.: 756,087

[22] Filed: Jan. 3, 1977

[51] Int. Cl.$^2$ .............................................. C23F 11/14
[52] U.S. Cl. ........................... 252/389 R; 21/2.5 R; 21/2.7 R; 106/14; 208/47; 252/8.55 E; 252/68; 252/387; 423/400
[58] Field of Search ............. 252/389 R, 387, 8.55 E, 252/68; 21/2.5 R, 2.7 R; 106/14; 208/47; 423/400

[56] References Cited

U.S. PATENT DOCUMENTS

| 3,433,577 | 3/1969 | Shick | 21/2.7 R |
| 3,925,245 | 12/1975 | Harris et al. | 252/387 |

*Primary Examiner*—Benjamin R. Padgett
*Assistant Examiner*—Irwin Gluck

[57] ABSTRACT

An oil dispersible rust inhibitor consisting of a chemical complex of a metal nitrite with a hetero-atomic aprotic polar organic solvent. Preferred metal nitrites are the alkali, alkaline earth metals or nickel, zinc, or cadmium nitrites. Preferred solvents are dimethylsulfoxide, dimethylformamide, dibutylformamide, n-methylpyrrolidone, dioxane, ethylcarbonate, tetrahydrofuran and their derivatives. The complex is prepared by reacting a nitrite ion with a solution of a basically reacting metal salt in the selected solvent. The excess metal salt is removed from the solution after completion of the reaction. The complex is readily solubilized in oil through the use of common dispersants.

18 Claims, No Drawings

NITRITE BASED RUST INHIBITOR COMPLEX

FIELD OF INVENTION

This invention relates to rust inhibitors and more particularly to nitrite based rust inhibitors which are readily dispersed in petroleum based compositions.

BACKGROUND OF THE INVENTION

Metal nitrites have been known for their rust inhibiting properties as used in aqueous solutions for a long time. The use of metal nitrites in organic composition has, however, been hindered by the insoluble nature of such nitrites in the organic media. Several attempts have been made to incorporate metal nitrites in organic compositions. Metal nitrites, in granular form have been mixed into organic compositions or lubricants and mechanically dispersed by milling or grinding. In such mechanical dispersions, the nitrite particle sizes are usually 5 microns or more and result in abrasion and wear of lubricated surfaces. Another method of mixing metal nitrites with lubricants is by the use of emulsifying agents. Such lubricating compositions are unstable, however, and the metal nitrite precipitates. Abrasive particles are thereby produced and again high rates of wear ensue. Obviously, such methods are unsuitable for present day lubricants and similar products which are used at high operating speeds and temperatures.

It is therefore an object of this invention to provide a form of metal nitrite which is readily dispersible in petroleum based lubricants such as grease and oil and other organic compositions.

It is a further object of this invention to provide dispersions of metal nitrite in a petroleum based composition where the metal nitrite is in a micellar form and does not precipitate out from the composition.

It is also an object of this invention to provide a dispersion of metal nitrite in petroleum based compositions which is non-abrasive to lubricated surfaces and does not contribute to accelerated wear.

It is yet another object of the invention to provide methods for producing such dispersible forms of metal nitrite.

It is a further object of the invention to provide a method for dispersing the above-mentioned dispersible nitrite compositions in petroleum based lubricants.

These and other objects, advantages and features of the invention will become apparent in the subsequent summary and detailed description of the invention.

SUMMARY OF THE INVENTION

The rust inhibitor of this invention consists of a chemical complex of a metal nitrite with a hetero-atomic aprotic polar organic solvent which is always a Lewis base. The solvent therefore has the following physical properties:

i. hetero-atomic — the organic compound contains at least a nitrogen, sulfur or oxygen atom; and ii. aprotic — the polar solvent has a moderately high dielectric constant and does not contain an acidic hydrogen.

These physical properties of the solvent are necessary to lend stability to and to permit formation of the rust inhibitor complex. The rust inhibitor complexes are readily dispersible in petroleum based compositions. The several complexes may be represented by the empirical formula:

$$M^{n+}(NO_2)_n L_z$$

wherein

M is the metal ion of the metal nitrite

L is the hetero-atomic aprotic polar organic solvent $n$ is an integer of 1 or 2

$z$ is equal to or greater than $n$

In a preferred embodiment of the invention, the metal may be selected from the group consisting of alkali metals, alkaline earth metals, nickel, zinc and cadmium. The polar organic solvent may be a member selected from the group of compounds consisting of dimethylsulfoxide, dimethylformamide, dibutylformamide, n-methylpyrrolidone, dioxane, ethyl carbonate, tetrahydrofuran and their various chemical derivatives.

A method for producing the chemical complex comprises reacting nitrous acid with a basically reacting metal salt in a medium consisting of a selected hetero-atomic aprotic polar organic solvent. The basically reacting metal salt provides the metal ion of the aforesaid metal nitrite complex. After the reaction is completed, the undissolved basically reacting metal salt is removed to give the desired complex in excess solvent. A concentrate of the complex may be formed by removing the excess solvent, such as by heating the solution under reduced pressure.

The nitrous acid may be prepared by passing an alkali metal nitrite dissolved in a medium of a hetero-atomic aprotic polar organic solvent and from 0 to 30 percent by weight of water, through an ion exchange column in hydrogen ion form at a temperature above the freezing point of the solution and below 10° C. In a preferred embodiment of this process of making nitrous acid, the polar solvent should be miscible with at least a small amount of water so that the metal nitrite can be dissolved in the solution because metal nitrites have very limited solubility in more polar solvents of the type defined above. With a preferred embodiment of this process it is desirable for the polar solvent to be miscible with a minimum of approximately 5 percent water so that solubility of the metal nitrite in the solvent is assured. The solution is passed through the ion exchange column to give an eluate of a solution of nitrous acid in the polar organic solvent.

The complex is readily dispersible in petroleum based compositions, such as lubricating oils, greases, brake fluid, automatic transmission fluid and similar products. Subsequent to dispersion of the complex in a composition, the stability of the complex precludes precipitation of abrasive nitrite crystals.

DETAILED DESCRIPTION OF THE PREFERRED EMBODIMENTS

It is understood that the following preferred embodiments are not to be interpreted as limiting the scope of the invention.

Although the structure of the nitrite based complex of this invention is not fully understood, it is believed that the stability of the complex is dependent upon the strength of the polar attraction between the metal nitrite and the polar solvent, i.e.: the Lewis base. This attraction stabilizes the complex so that subsequent to dispersion of the complex in a petroleum based composition the metal nitrite remains in solution and does not precipitate in the form of abrasive crystals.

In the empirical formula $M^{n+}(NO_2)_n L_z$, it was discovered by quantitative analysis of the complex that for a given value of $n$, the following relationship between $n$ and $z$ existed $Z$ is equal to or greater than $n$ Preferred solvents are dimethylformamide, dibutylformamide, dimethylsulfoxide, n-methylpyrrolidone and their chemical derivatives. The preferred metal nitrites are calcium, magnesium and barium.

The chemical complex according to this invention can be concentrated by removal of excess solvent preferably by distillation. When concentrated, it will contain approximately 0.4 to 15% by weight of nitrite ions. When dispersed in the finished lubricant or rust preventive composition the concentration of nitrite will usually be between 0.07 and 2.0% by weight.

In the most preferred embodiment of this invention, an ion exchange column containing an "AMBERLITE" (trademark) resin in the hydrogen ion form is used to prepare nitrous acid. The temperature of the column should be maintained above the freezing point of the eluate but no higher than 10° C. At temperatures higher than this, the nitrous acid in the column breaks down to give off nitrogen oxide fumes which are hazardous and undesirable. A selected metal nitrite is dissolved in a solvent/water mixture. The selection of the solvent is predetermined by the desired complex, e.g., if a dimethylformamide complex is desired, then dimethylformamide is used as the solvent. The amount of water in the solvent/water mixture is preferably approximately 10 to 25 percent of the mixture. Use of excessive amounts of water in the solvent/water mixture results in the nitrite precipitating during subsequent reaction with the basically reacting metal salt. The residence time in the ion exchange column should be sufficient to permit a total exchange of the hydrogen ion for the metal ion to provide nitrous acid in the eluate.

The eluate is immediately mixed with a selected basically reacting metal salt usually in a slurry form with a selected solvent. The slurry is preferably made by mixing equal parts of the desired basically reacting metal salt and the solvent and continuing mixing while the nitrous acid in the eluate reacts with the basically reacting metal salt and solvent to form the desired complex. Any undissolved metal salt is removed from the solution by filtration. The filtrate may be added to a petroleum based lubricant to provide rust-inhibitive properties therein. However, it is desirable to concentrate the solution prior to incorporation of the complex into a lubricant.

The excess solvent may be removed from the solution by distillation under reduced pressure and continuing evaporation until most of the excess solvent is removed to give an oily viscous product. That portion of solvent which is part of the complex does not evaporate during removal of excess solvent. For example, in the production of a complex of calcium nitrite with dimethylformamide, the solution containing the complex in excess dimethylformamide was subjected to heating at 105° C under 10 mm Hg absolute pressure to drive off the excess solvent. The resultant product contained 28 percent by weight nitrite, 11.6 percent calcium and 58.3 percent dimethylformamide. The analysis for the nitrite was carried out spectrophotometrically, the analysis for calcium was carried out titrimetrically and the analysis for the solvent was carried out by the Kjeldahl nitrogen analysis.

Another method for preparing the chemical complex of this invention is to bubble dinitrogen trioxide gas through a slurry of a basically reacting metal salt in a selected polar organic solvent. After bubbling the $N_2O_3$ through the slurry, the slurry is filtered to give a solution containing the complex. Excessive dinitrogen trioxide is undesirable due to the formation of other nitrogen oxides. The solution may be concentrated by heating under reduced pressure to remove the excess solvent.

The concentrates of the complexes may be incorporated in organic media and lubricants by dispersing them in commonly used oil soluble additives which are subsequently added to the final retail oil product. (For example, the complex may be dispersed in alkylsuccinimides, alkylarylphenates and alkylarylsulphonates which are commonly used in the oil additives industry.)

The following examples are illustrative of methods for preparing the complexes according to this invention.

EXAMPLE 1

Preparation of Complex by Ion Exchange Method 15 parts by weight of $NaNO_2$ were dissolved in 185 parts by weight of a 9 : 1 dimethylformamide/water mixture. The solution was passed through an ion exchange column of "AMBERLITE" resin in the hydrogen form. The column temperature was maintained at 2° to 10° C. The eluate of $HNO_2$ in the 9 : 1 dimethylformamide/water mixture was immediately reacted with agitation in a slurry of 15 parts by weight of $Ca(OH)_2$ and 15 parts by weight of dimethylformamide. Elution of the column was continued until the eluate was at a pH of about 7. The slurry was then filtered to remove undissolved $Ca(OH)_2$. The excess solvents were removed from the filtrate by heating the filtrate to 140° C under a pressure of 250 mm Hg. absolute to give an oily, viscous concentrate consisting of a complex of calcium nitrite with dimethylformamide. The concentrate containing the chemical complex analyzed 27% nitrite ion, 11.2% calcium ion and 61.5% dimethylformamide.

Similarly, other complexes according to the invention may be prepared by this method by selecting the appropriate basically reacting metal salt and polar organic solvent, the selection being predetermined by the desired complex.

EXAMPLE 2

In the process of Example 1, a potassium nitrite was substituted for the sodium nitrite to give an eluate containing $HNO_2$.

EXAMPLE 3

Preparation of Complex by Using $N_2O_3$ 20 parts by weight of Ca $(OH)_2$ were mixed in 200 parts by weight of dimethylformamide. $N_2O_3$ was bubbled through the mixture at a rate of 325 mls. per minute for 4 hours. The solution was filtered to remove excess Ca $(OH)_2$ to give a complex of calcium nitrite with dimethylformamide. The analyzed product contained 4.5% nitrite, 4.4% calcium and 91.1% dimethylformamide.

EXAMPLE 4

In the process of Example 3, 20 parts of Ca $(OH)_2$ were mixed with 200 parts of N-methylpyrrolidone to give a complex of calcium nitrite with N-methylpyrrolidone.

Similarly, other complexes according to this invention may be prepared by the process of Example 3 by selecting the appropriate basically reacting metal salt and polar organic solvent, the selection being predetermined by the desired complex.

EXAMPLE 5

Dispersion of Complex Concentrate in an Oil

To a heated mixture of 50 parts of alkylsuccinimide and 100 parts of lubricating oil (S.U.S. 100) and 150 parts xylene, 200 parts of the concentrated complex of calcium nitrite with dimethylformamide of Example 1 were added slowly over half an hour at 66° C. After complete addition, 10 parts water were added over 10 minutes to reduce the viscosity of the mixture. The mixture was stirred for half an hour followed by azeotropic removal of the water. The remaining excess solvents were removed under vacuum. The resultant oil additive contained 5% by weight of nitrite.

Other complexes of calcium, magnesium and barium nitrite with dimethylformamide and dimethylsulfoxide were dispersed in combinations of alkylarylsulphonates and alkylsuccinimide.

EXAMPLE 6

To 45 parts of concentrated complex of calcium nitrite with dimethylformamide of Example 1, 150 parts of dodecyl phenol were added at 150° C. The mixture was heated to 200° C under vacuum to remove the excess dimethylformamide. The resultant oil additive contained 4% by weight of nitrite.

Similarly, the other complexes of the Examples may be dispersed in an alkylated phenol based oil additive.

The rust inhibitive properties of the nitrite based complexes according to this invention were evaluated by various well known tests as defined in the following Tables I, II and III. The chemical complexes tested were prepared by the methods of Examples 1, 2 and 3. The solution containing the complex prepared by Example 3 was concentrated by heating under reduced pressure in a manner similar to that of Example 1 to give a concentrate of the complex.

TABLE I

Test ASTM-D1743 - RUST PREVENTIVE PROPERTIES OF LUBRICATING GREASES
Grease Base - NLGI#2 Lithium 12 Hydroxy Stearate Grease

| Test No. | Additive | Rating | | |
|---|---|---|---|---|
| 1 | none | #3 | #3 | #3 |
| 2 | 1% of complex of Example 1 (.28% NO$_2$) | #3 | #3 | #3 |
| 3 | 5% of complex of Example 1 (1.4% NO$_2$) | #1 | #1 | #2 |

Ratings: #1 Pass, #2 Incipient Corrosion, #3 Fail

TABLE II

ASTM-D665B - STEAM-TURBINE OIL RUST TEST
Base Oil Used - Solvent Refined Neutral Oil of 100 SUS at 100° F.

| Test No. | Additive | Concentration | Result |
|---|---|---|---|
| 1 | complex calcium nitrite/dimethyl-formamide | .1% | pass |
| 2 | complex calcium nitrite/dimethyl-formamide | 0.06% | moderate rusting |
| 3 | complex calcium nitrite/dimethyl-sulfoxide | .3% | pass |
| 4 | complex calcium nitrite/dimethyl-sulfoxide | .2% | severe rusting |
| 5 | complex calcium nitrite/N-methylpyrrolidone | .15% | pass |
| 6 | complex calcium nitrite/N-methylpyrrolidone | .1% | moderate rusting |
| 7 | complex magnesium nitrite/dimethyl-formamide | .15% | pass |
| 8 | complex magnesium nitrite/dimethyl-formamide | .1% | moderate rusting |
| 9 | complex barium nitrite/dimethyl-formamide | .15% | pass |
| 10 | complex barium nitrite/dimethyl-formamide | .1% | moderate rusting |

TABLE III

CLEVELAND CONDENSING HUMIDITY CABINET TEST
Base Oil Used - Solvent Refined Neutral Oil of 100 SUS at 100° F.

| Test No. | Additive | Concentration | Result % rust time (hrs) | |
|---|---|---|---|---|
| 1 | complex calcium nitrite/dimethylsulfoxide | 2% NO$_2$ in test composition | 30 | 40 |
| 2 | complex calcium nitrite dimethylsulfoxide | 0.3% NO$_2$ in test composition | 100 | 40 |
| 3 | Nasul BSN * (trademark) | 20% of additive in test composition | 100 | 20 |
| 4 | Surchem 301 * (trademark) | 20% of additive in test composition | 100 | 20 |
| 5 | Nuodex 545 * (trademark) | 20% of additive in test composition | 100 | 40 |

* commercial rust inhibitors: #3 sold through R.T. Vanderbilt Co. Inc., Connecticut; #4 sold through Surpass Chemicals Ltd., Canada; #5 sold through Nuodex Canada Ltd., Canada The results of the tests shown in Tables I, II and III establish that the nitrite based complexes according to this invention provide satisfactory rust inhibiting properties in lubricants. When the rust inhibitive properties of the complex of calcium nitrite with dimethylsulfoxide were compared to commercially known rust inhibitors such as Nasul BSN and Nuodex 545 in Table III, it was noted that the complex has superior properties even at concentrations as low as 0.3% NO$_2$ in the lubricant.

Although various preferred embodiments of the invention have been described herein in detail, it is understood by those skilled in the art that variations may be made thereto without departing from the spirit of the invention or the scope of the appended claims.

The embodiments of the invention in which an exclusive property or privilege is claimed are defined as follows:

1. A rust inhibitor which is dispersible in petroleum based compositions consisting of a complex of a metal nitrite with a hetero-atomic aprotic polar organic solvent, which is miscible with at least 5% water and the hetero-atom being nitrogen, sulfur or oxygen; said complex being represented by the empirical formula:

$$M^{n+}(NO_2)_n L_z$$

wherein

M is a metal ion of said metal nitrite
L is said hetero-atomic aprotic polar organic solvent
$n$ is an integer of 1 or 2, and
$z$ is equal to or greater than $n$.

2. Dispersions of the rust inhibitor of claim 1 in petroleum based compositions.

3. A rust inhibitor of claim 1 wherein said metal nitrite is selected from the group of compounds consisting of alkali metal nitrites, alkaline earth metal nitrites, nickel nitrite, zinc nitrite and cadmium nitrite.

4. A rust inhibitor of claim 1 wherein said solvent is selected from the group of compounds consisting of dimethylsulfoxide, dimethylformamide, dibutylformamide, N-methylpyrrolidone, dioxane, ethyl carbonate and tetrahydrofuran.

5. A rust inhibitor of claim 1 wherein said metal nitrite is selected from the group of compounds consisting of alkaline earth metal nitrites.

6. A rust inhibitor of claim 5 wherein said solvent is selected from the group of compounds consisting of dimethylsulfoxide, dimethylformamide, N-methylpyrrolidone and dibutylformamide.

7. A nitrite based rust inhibitor which is dispersible in a petroleum based composition consisting of a complex of calcium nitrite with a solvent selected from the group of compounds consisting of dimethylformamide, N-methylpyrrodidone, dimethylsulfoxide and dibutylformamide, there being a minimum of 2 moles of nitrite per mole of calcium.

8. A method for producing a nitrite based rust inhibitor which is dispersible in a petroleum based composition comprising reacting nitrous acid with a basically reacting metal salt in a medium consisting of a heteroatomic aprotic polar organic solvent which is miscible with at least 5% water and the hetero-atom being nitrogen, sulfur or oxygen, and removing excess basically reacting metal salt after completion of the reaction to give a solution containing the desired nitrite based rust inhibitor.

9. A method of claim 8 wherein said basically reacting metal salt is a metal hydroxide selected from the group of compounds consisting of alkaline earth metal hydroxides, alkali metal hydroxides, and nickel, zinc and cadmium hydroxides.

10. A method of claim 8 wherein said basically reacting metal salt is a metal hydroxide selected from the group of compounds consisting of alkaline earth metal hydroxides.

11. A method of claim 8 wherein said basically reacting metal salt is a metal oxide selected from the group of compounds consisting of alkaline earth metal oxides.

12. A method of claim 8 wherein said solvent is selected from the group of compounds consisting of dimethylsulfoxide, dimethylformamide, N-methylpyrrolidone, dibutylformamide, dioxane, ethyl carbonate, and tetrahydrofuran.

13. A method of claim 10 wherein said solvent is selected from the group of compounds consisting of dimethylsulfoxide, dimethylformamide, N-methylpyrrolidone, and dibutylformamide.

14. A method of claim 13 wherein the selected alkaline earth metal hydroxide is calcium hydroxide.

15. A method of claim 8 wherein said nitrous acid is prepared by passing a solution of sodium nitrite or potassium nitrite in a medium consisting of said solvent and up to 30 percent by weight of water through an ion exchange column in hydrogen ion form at a temperature above the freezing point of said solution and below 10° C to provide a source of nitrous acid in the eluate.

16. A method of claim 15 wherein a solution of sodium nitrite in a dimethylformamide/water medium is passed through an ion exchange column in hydrogen ion form.

17. A method of claim 16 wherein the amount of dimethylformamide in said medium is from 75 to 90 percent by weight of said medium, the concentration of sodium nitrite in said solution ranging from 7 percent by weight of the solution up to saturation.

18. A method of claim 16 wherein the eluate is reacted immediately with calcium hydroxide in a medium of dimethylformamide.

* * * * *